United States Patent
Nilsen et al.

(10) Patent No.: US 9,475,769 B2
(45) Date of Patent: Oct. 25, 2016

(54) ZINC HALIDE MEDIATED CYCLIZATION PROCESS LEADING TO TRICYCLIC INDOLES

(71) Applicant: GE Healthcare Limited, Buckinghamshire (GB)

(72) Inventors: Sondre Nilsen, Oslo (NO); Umamaheshwar P. Mokkapati, Andhra Pradesh (IN)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 14/648,618

(22) PCT Filed: Nov. 29, 2013

(86) PCT No.: PCT/EP2013/075107
§ 371 (c)(1),
(2) Date: May 29, 2015

(87) PCT Pub. No.: WO2014/083163
PCT Pub. Date: Jun. 5, 2014

(65) Prior Publication Data
US 2015/0336891 A1    Nov. 26, 2015

(30) Foreign Application Priority Data

Nov. 30, 2012  (IN) ............................ 3690/DEL/2012
Jan. 15, 2013  (GB) .................................. 1300649.9

(51) Int. Cl.
*C07D 209/88* (2006.01)

(52) U.S. Cl.
CPC .................................. *C07D 209/88* (2013.01)

(58) Field of Classification Search
CPC .................................................... C07D 209/88
See application file for complete search history.

(56) References Cited

FOREIGN PATENT DOCUMENTS

| CN | 1253948 A | 5/2000 |
|---|---|---|
| CN | 102448933 A | 5/2012 |
| EP | 0950657 | 10/1999 |
| WO | 9925340 | 5/1999 |
| WO | 03014082 | 2/2003 |
| WO | 03016277 | 2/2003 |
| WO | 2010109007 | 9/2010 |

OTHER PUBLICATIONS

Search Report, GB Application No. 1300649.9, search date May 14, 2013.
Search Report, Intl Application No. PCT/EP2013/075107, mail date Feb. 18, 2014.
Davies et al., Mapping the Melatonin Receptor. 5. Melatonin Agonists and Antagonists Derived from Tetrahydrocyclopent[b]indoles, Tetrahydrocarbazoles and Hexahydrocyclohept[b]indoles, J Med. Chem. 41:451-467 (1998).
Office Action and Search Report issued in Chinese Patent Office for counterpart Appl. No. 201380062464.9 filed Nov. 29, 2013. (English Translations enclosed).

*Primary Examiner* — Shawquia Jackson
(74) *Attorney, Agent, or Firm* — Wood IP LLC

(57) ABSTRACT

The present invention relates to a method for the production of tricyclic indole compounds comprising a cyclization step wherein this step is improved over known methods.

15 Claims, No Drawings

ZINC HALIDE MEDIATED CYCLIZATION PROCESS LEADING TO TRICYCLIC INDOLES

TECHNICAL FIELD OF THE INVENTION

The present invention relates to a chemical method and in particular to a chemical method to obtain a tricyclic indole compound. The method of the invention can be applied in the synthesis of tricyclic indole compounds that find use as pharmaceuticals and as radiopharmaceuticals.

DESCRIPTION OF RELATED ART

Tricyclic indole compounds are known in the art and have been reported to have activity as melatonin antagonists (Davies 1998 J Med Chem; 41: 451-467), secretory phospholipase $A_2$ inhibitors (Anderson et al EP 0952149 A1), treatment for Alzheimer's disease (Wantanabe WO 99/25340), treatment of inflammatory diseases such as septic shock (Kinnick et al WO 03/014082 and WO 03/016277) and high binding affinity to translocator protein (TSPO, formerly known as peripheral benzodiazepine receptor; Wadsworth et al (WO 2010/109007).

One reported method for the synthesis of these tricyclic indole compounds broadly comprises a condensation reaction between an analine and a bromo oxocycloalkanecarboxylate, followed by cyclization in the presence of zinc chloride.

Davies et al (J Med Chem 1998; 41: 451-467) describe melatonin agonists and antagonists derived from tetrahydrocyclopent[b]indoles, tetrahydrocarbazoles and hexahydrocyclohept[b]indoles. The general mechanism presented in this paper for the synthesis of these compounds comprises treating the appropriate N-methylaniline with the appropriate 3-bromo-2-oxocycloalkanecarboxylate as shown below followed by reaction with zinc chloride and heating for 16 hours:

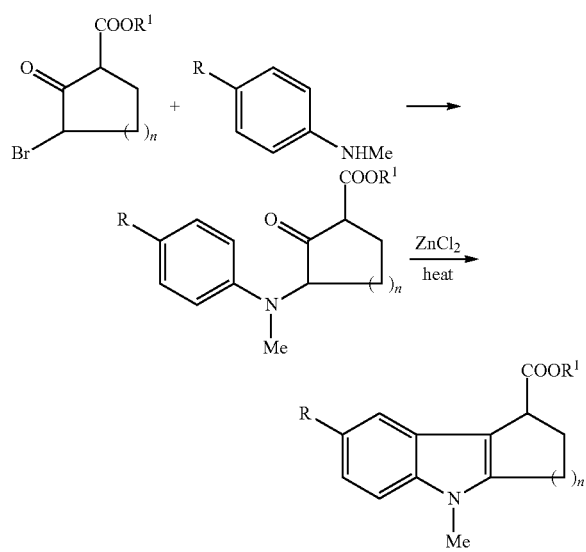

In the above scheme, Me is methyl and the variables R, $R^1$ and n are as defined by Davies et al, supra. Following the cyclization reaction, the product was extracted three times with a mixture of hydrochloric acid and ethyl acetate, washed with water and $Na_2CO_3$, dried with $MgSO_4$ followed by evaporation of the solvent to obtain the ester in sufficient purity to be used in subsequent reactions.

Kinnick et al (WO 2003/014082) describe tricyclic indole compounds and a synthesis method for their preparation comprising condensation of 2-carbomethoxy-5-bromocyclopentanone and N-benzyl-2-chloro-5-methoxyaniline, followed by heating with zinc chloride at reflux temperature over a period of 10-60 hours:

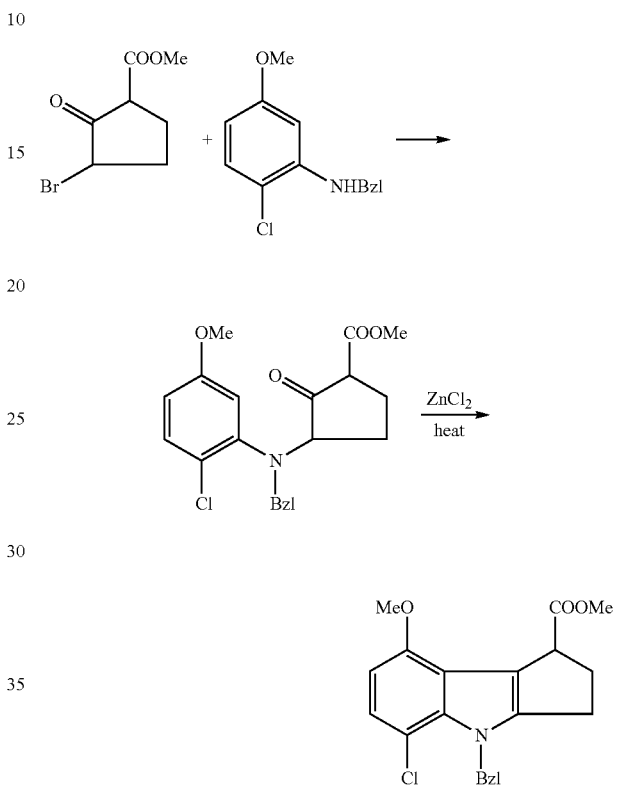

In the above scheme Me is methyl and Bzl is benzyl. Following the cyclization the reaction mixture was cooled, concentrated in vacuo and purified by chromatography. This reaction was adapted by the same group to obtain the heptane derivative, substituting the 2-carbomethoxy-5-bromocyclopentanone of the scheme above with 2-carbomethoxy-5-bromocycloheptanone (Kinnick et al WO 2003/016277), followed by cooling, filtration, washing, drying and concentration in vacuo. More specifically for this heptane derivative, Kinnick et al made 2 separate additions of $ZnCl_2$: 1M $ZnCl_2$ in diethyl ether added to the intermediate dissolved in toluene, and then another 1M $ZnCl_2$ in diethyl ether added after 1 hour along with further toluene.

Anderson et al (EP0952149 B1) describe substituted carbazoles wherein the preparation of certain of these compounds comprises condensation of 2-carbethoxy-6-bromocyclohexanone with an aniline followed by addition of zinc chloride and refluxing in benzene. Following the cyclization step, the residue worked up before being taken to the subsequent step, e.g. in one example the residue was taken up in ethyl acetate, washed with hydrochloric acid, washed with water, dried over sodium sulfate, evaporated in vacuo and then purified by silica gel chromatography.

Wadsworth et al (WO 2010/109007) describe the synthesis of $^{18}F$-labelled tricyclic compounds using similar methods according to the following scheme:

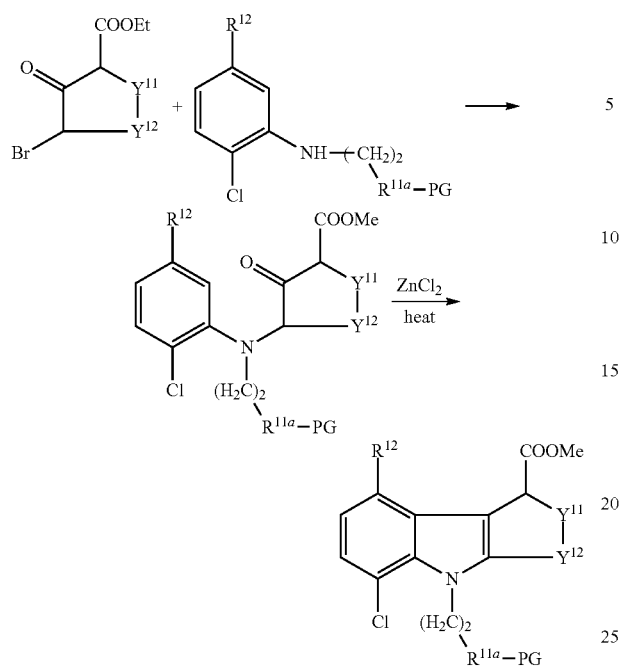

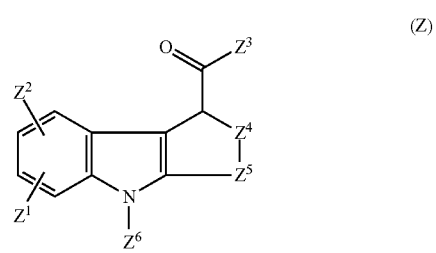

In the above Et is ethyl and PG is a protecting group and the variables $Y^{11}$, $Y^{12}$, $R^{11a}$ and $R^{12}$ are defined therein. In the experimental examples, following the cyclization step, the reaction was dissolved in ethyl acetate, washed with hydrochloric acid and potassium carbonate (and in some cases also water), dried over magnesium sulphate, concentrated in vacuo and in some cases also purified by silica gel chromatography.

The present inventors have found that the above-described methods present difficulties during the cyclization reaction and/or require re-work of the cyclized product before any subsequent reactions to be carried out, which can be time-consuming and labour-intensive. There is therefore a need for improved methods for carrying out this cyclization reaction.

SUMMARY OF THE INVENTION

The present invention relates to a method for the production of tricyclic indole compounds comprising a cyclization step wherein this step is improved over known methods. The present inventors have observed that the zinc halide reagent used for the cyclization appears to deactivate itself over time. The inventive method proposes to add the zinc halide using multiple additions at defined timepoints. With the method of the invention it is not required to separate the two phases formed during the cyclization reaction and carry out a re-work of one of the phases in order to result in an acceptable yield. The lot-wise addition of zinc halide during cyclization has been observed to facilitate better conversion, thereby improving yield and avoiding significant rework of the cyclized product.

DETAILED DESCRIPTION OF THE PREFERRED EMBODIMENTS

In one aspect the present invention provides a method for the production of a compound of Formula Z:

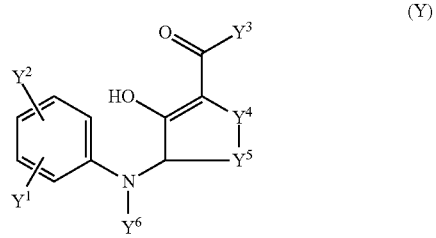

wherein:
$Z^1$ is an $R^1$ group selected from halo or $C_{1-3}$ alkyl;
$Z^2$ is an $R^2$ group selected from hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy;
$Z^3$ is an $R^3$ group selected from $C_{1-6}$ alkyl or —O—$R^7$ wherein $R^7$ is $C_{1-6}$ alkyl;
$Z^4$ is an $R^4$ group selected from O, S, SO, $SO_2$ or $CH_2$;
$Z^5$ is an $R^5$ group selected from $CH_2$, $CH_2$—$CH_2$, $CH(CH_3)$—$CH_2$ or $CH_2$—$CH_2$—$CH_2$;
$Z^6$ is an $R^6$ group selected from $C_{1-10}$ alkyl or an amine protecting group, or $R^6$ is the group —O—$R^8$ wherein $R^8$ is $C_{1-10}$ alkyl, $C_{3-12}$ aryl, $C_{7-14}$ arylalkyl or a hydroxyl protecting group;
wherein said method comprises cyclizing of a compound of Formula Y:

(Y)

wherein each of $Y^{1-6}$ are the same as each of $Z^{1-6}$;
wherein said cyclizing is carried out by introduction of a zinc halide in a suitable solvent to a solution of said compound of Formula Y wherein said introduction comprises a first addition and a second addition carried out at least 6 hours after said first addition.

The term "halo" or "halogen" is taken to mean any one of chloro, fluoro, bromo or iodo.

The term "alkyl" used either alone or as part of another group is defined as any straight —$C_nH_{2n+1}$ group, branched —$C_nH_{2n+1}$ group wherein n is >3, or cyclic —$C_nH_{2n-1}$ group where n is >2. Non-limiting examples of alkyl groups include methyl, ethyl, propyl, isobutyl, cyclopropyl and cyclobutyl.

The term "hydroxyl" refers to the group —OH.

The term "cyano" refers to the group —CN.

The term "alkoxy" refers to an alkyl group as defined above comprising an ether linkage, and the term "ether linkage" refers to the group —C—O—C—. Non-limiting examples of alkoxy groups include, methoxy, ethoxy, and propoxy.

The terms "fluoroalkyl" and "fluoroalkoxy" refer respectively to an alkyl group and an alkoxy group as defined above wherein a hydrogen is replaced with a fluoro.

The term "aryl" refers to any molecular fragment or group which is derived from a monocyclic or polycyclic aromatic hydrocarbon, or a monocyclic or polycyclic heteroaromatic hydrocarbon.

The term "arylalkyl" refers to an aryl-substituted alkylene group wherein aryl and alkylene are as defined above.

The term "protecting group" is meant a group which inhibits or suppresses undesirable chemical reactions, but which is designed to be sufficiently reactive that it may be cleaved from the functional group in question to obtain the desired product under mild enough conditions that do not modify the rest of the molecule. Protecting groups are well-known in the art and are discussed in detail in 'Protective Groups in Organic Synthesis', by Greene and Wuts (Fourth Edition, John Wiley & Sons, 2007).

Non-limiting examples of suitable protecting groups for hydroxyl include methyl, ethyl, isopropyl, allyl, t-butanyl, benzyl (—$CH_2C_6H_5$), benzoyl (—$COC_6H_5$), and for ester groups include t-butyl, ester benzyl ester, isopropyl, and methyl and ethyl esters.

The term "cyclizing" refers to the formation of a cyclic compound from an open-chain compound.

A "zinc halide" is suitably selected from zinc chloride and zinc bromide and is preferably zinc chloride.

The "suitable solvent" for said zinc halide is selected from diethyl ether, propan-2-ol, toluene, tetrahydrofuran (THF), 2-methyl-THF (MTHF) and cyclopentylmethylether (CPME).

Said $R^1$ group is preferably at the bottom position (i.e. the 8 position of either Formula Y or Z) of the aryl ring to which it is attached.

Said $R^2$ group is preferably at the top position (i.e. the 5 position of either Formula Y or Z) of the aryl ring to which it is attached.

Said $R^1$ group is preferably halo and is most preferably chloro.

Said $R^2$ group is preferably $C_{1-3}$ alkoxy, $C_{1-3}$ or $C_{1-3}$ fluoroalkoxy, most preferably $C_{1-3}$ alkoxy and most especially preferably methoxy.

Said $R^3$ group is preferably —O—$R^7$ wherein $R^7$ is $C_{1-6}$ alkyl, preferably wherein $R^7$ is $C_{1-3}$ alkyl and most preferably wherein $R^7$ is ethyl.

Said $R^4$ group is preferably S, SO, $SO_2$ or $CH_2$ and is most preferably $CH_2$.

Said $R^5$ group is preferably $CH_2$, $CH_2$—$CH_2$, or $CH_2$—$CH_2$—$CH_2$ and is most preferably $CH_2$—$CH_2$.

Said $R^6$ group is preferably $C_{1-10}$ alkyl or an amine protecting group. Alternatively preferably said $R^6$ group is the group —O—$R^8$ wherein $R^8$ is $C_{1-10}$ alkyl, $C_{3-12}$ aryl, $C_{7-14}$ arylalkyl or a hydroxyl protecting group. In this alternative preferred embodiment $R^8$ is preferably a hydroxyl protecting group and most preferably is benzyl.

For a preferred compound of either Formula Y or Formula Z:

Said $R^1$ group is halo;
Said $R^2$ group is $C_{1-3}$ alkoxy, $C_{1-3}$ or $C_{1-3}$ fluoroalkoxy;
Said $R^3$ group is —O—$R^7$ wherein $R^7$ is $C_{1-6}$ alkyl;
Said $R^4$ group is S, SO, $SO_2$ or $CH_2$;
Said $R^5$ group is $CH_2$, $CH_2$—$CH_2$, or $CH_2$—$CH_2$—$CH_2$; and,
Said $R^6$ group is $C_{1-10}$ alkyl or an amine protecting group.

For an alternative preferred compound of either Formula Y or Formula Z:

Said $R^1$ group is halo;
Said $R^2$ group is $C_{1-3}$ alkoxy, $C_{1-3}$ or $C_{1-3}$ fluoroalkoxy;
Said $R^3$ group is —O—$R^7$ wherein $R^7$ is $C_{1-6}$ alkyl;
Said $R^4$ group is S, SO, $SO_2$ or $CH_2$;
Said $R^5$ group is $CH_2$, $CH_2$—$CH_2$, or $CH_2$—$CH_2$—$CH_2$; and,
Said $R^6$ group is the group —O—$R^8$ wherein $R^8$ is $C_{1-10}$ alkyl, $C_{3-12}$ aryl, $C_{7-14}$ arylalkyl or a hydroxyl protecting group.

For a most preferred compound of either Formula Y or Formula Z:

Said $R^1$ group is at the bottom position of the aryl ring to which it is attached and is halo;
Said $R^2$ group is at the top position of the aryl ring to which it is attached and is $C_{1-3}$ alkoxy, $C_{1-3}$ or $C_{1-3}$ fluoroalkoxy;
Said $R^3$ group is —O—$R^7$ wherein $R^7$ is $C_{1-3}$ alkyl;
Said $R^4$ group is $CH_2$;
Said $R^5$ group is $CH_2$—$CH_2$; and,
Said $R^6$ group is the group —O—$R^8$ wherein $R^8$ is a hydroxyl protecting group.

For an especially preferred compound of either Formula Y or Formula Z:

Said $R^1$ group is at the bottom position of the aryl ring to which it is attached and is chloro;
Said $R^2$ group is at the top position of the aryl ring to which it is attached and is $C_{1-3}$ alkoxy;
Said $R^3$ group is —O—$R^7$ wherein $R^7$ is ethyl;
Said $R^4$ group is $CH_2$;
Said $R^5$ group is $CH_2$—$CH_2$; and,
Said $R^6$ group is the group —O—$R^8$ wherein $R^8$ is benzyl.

For a most especially preferred compound of either Formula Y or Formula Z:

Said $R^1$ group is at the bottom position of the aryl ring to which it is attached and is chloro;
Said $R^2$ group is at the top position of the aryl ring to which it is attached and is methoxy;
Said $R^3$ group is —O—$R^7$ wherein $R^7$ is ethyl;
Said $R^4$ group is $CH_2$;
Said $R^5$ group is $CH_2$—$CH_2$; and,
Said $R^6$ group is the group —O—$R^8$ wherein $R^8$ is benzyl.

It is an essential feature of the present invention that the zinc halide is introduced using more than one addition. The present inventors have found in addition that second and subsequent additions of zinc halide are suitably carried out at least 6 hours after the previous addition. If subsequent additions of zinc halide are made too early, the present inventors have faced significant problems stirring the reaction, which is assumed to be due to precipitation of zinc halide. Addition of zinc halide can in another embodiment further comprise a third addition wherein said third addition is carried out at least 6 hours after said second addition. Preferably, the time between each addition is from 6-36 hours, most preferably from 12-24 hours. The quantity of zinc halide added at each addition is also important. Preferably, a significant surplus is used in the first addition with half the amount of the first addition for each subsequent addition, e.g. around a gram of zinc halide per gram of uncyclized intermediate (i.e. compound of Formula Y) for the first addition and around half a gram per gram of uncyclized intermediate for each subsequent addition. In one embodiment, >3 molar equivalents can be used with the first addition.

Compounds of Formula Y can be obtained from commercial starting materials using or adapting methods described in the prior art. Reference is made in this regard to the teachings of Julia & Lenzi (Bulletin de la Societé de France 1962: 2262-2263), Davies et al (J Med Chem 1998; 41: 451-467), Kinnick et al (WO 2003/014082 and WO 2003/016277), Anderson et al (EP0952149 B1) and Wadsworth et al (WO 2010/109007). In each of these publications compounds of Formula Y are obtained by condensation reaction between an analine and a bromo oxocycloalkanecarboxylate as illustrated in Scheme 1 below:

Scheme 1

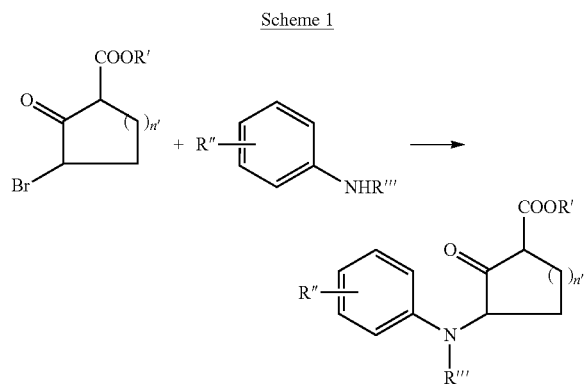

In the above scheme R' is an $R^7$ group as defined herein, R" is an $R^1$ and/or an $R^2$ group as defined herein, R'" is an $R^6$ group as defined herein and n' is an integer of 1-3.

The compounds of Formula Z obtained by the above-described method of the invention may be further converted by means well-known to those of skill in the art to obtain additional compounds. Therefore, in another embodiment, the method of the present invention further comprises conversion of the group —C(=O)—$Z^3$ of Formula Z to the group —C(=O)—$Z^{13}$ wherein $Z^{13}$ is hydroxyl or $NR^9R^{10}$ wherein $R^9$ and $R^{10}$ are independently $C_{1-3}$ alkyl, $C_{7-10}$ arylalkyl, or $R^9$ and $R^{10}$, together with the nitrogen to which they are attached, form a nitrogen-containing $C_{4-6}$ aliphatic ring optionally comprising 1 further heteroatom selected from nitrogen, oxygen and sulphur.

A "nitrogen-containing $C_{4-6}$ aliphatic ring" is a saturated $C_{4-6}$ alkyl ring comprising a nitrogen heteroatom. Examples include pyrolidinyl, piperidinyl and morpholinyl rings.

This further step can be easily achieved using well-known synthetic chemistry techniques. For example, where $Z^3$ in the group —C(=O)—$Z^3$ is —O—$R^7$ it can be converted to —C(=O)—$Z^{13}$ wherein $Z^{13}$ is hydroxyl by straightforward removal of the $R^7$ group by hydrolysis using an acid or a base, preferably by using a base such as NaOH.

In another embodiment, the method of the present invention further comprises conversion of the group —N—$Z^6$ to the group —N—$Z^{16}$ wherein $Z^{16}$ is hydrogen, $C_{1-10}$ alkylene-OH or $C_{1-10}$ alkylene-LG wherein LG is a leaving group.

The term "alkylene" refers to a divalent linear —$C_nH_{2n}$— group.

The term "leaving group" refers to a molecular fragment that departs with a pair of electrons in heterolytic bond cleavage. Non-limiting examples of suitable leaving groups include halo groups selected from chloro, iodo, or bromo, aryl or alkyl sulfonates such as tosylate, triflate, nosylate or mesylate.

$Z^{16}$ is preferably $C_{1-10}$ alkylene-LG and most preferably $C_{1-6}$ alkylene-LG.

LG is preferably halo, or an aryl or alkyl sulfonate, and is most preferably an aryl or alkyl sulfonate. Preferred aryl or alkyl sulfonates are selected from tosylate, triflate, nosylate and mesylate.

Conversion of the group —N—$Z^6$ to the group —N—$Z^{16}$ can be carried out in a straightforward manner, e.g. by simply removing a protecting group in order to obtain —$NH_2$ or —N-alkylene-OH, and by further reacting with a suitable source of a leaving group to obtain —N-alkylene-LG. Suitable sources of leaving groups are commercially available and well-known to those skilled in the art, e.g. sulfonyl chloride reagents such as p-toluenesulfonyl chloride (TsCl) and methanesulfonyl chloride (MsCl).

In a yet further embodiment, the method of the invention further comprises conversion of the group —N—$Z^{16}$ to the group —N—$Z^{26}$ wherein $Z^{26}$ is $C_{1-10}$ alkylene-$^{18}$F.

Labelling with $^{18}$F can be achieved by nucleophilic displacement of LG in one step by reaction with a suitable source of [$^{18}$F]-fluoride ion ($^{18}$F), which is normally obtained as an aqueous solution from the nuclear reaction $^{18}$O(p,n)$^{18}$F and is made reactive by the addition of a cationic counterion and the subsequent removal of water. $^{18}$F can also be introduced by O-alkylation of hydroxyl groups with $^{18}$F(CH$_2$)$_3$-LG wherein LG is as defined above.

[$^{18}$F]-radiotracers are now often conveniently prepared on an automated radiosynthesis apparatus. There are several commercially-available examples of such apparatus, including Tracerlab™ and Fastlab™ (GE Healthcare Ltd). Such apparatus commonly comprises a "cassette", often disposable, in which the radiochemistry is performed, which is fitted to the apparatus in order to perform a radiosynthesis. The cassette normally includes fluid pathways, a reaction vessel, and ports for receiving reagent vials as well as any solid-phase extraction cartridges used in post-radiosynthetic clean up steps. In a preferred embodiment therefore the further step of conversion of the group —N—$Z^{16}$ to the group —N—$Z^{26}$ wherein $Z^{26}$ is $C_{1-10}$ alkylene-$^{18}$F is automated.

The following non-limiting examples serve to illustrate the invention in more detail.

BRIEF DESCRIPTION OF THE EXAMPLES

Example 1 describes how the method of the present invention can be carried out to obtain a compound of Formula Z by cyclizing a compound of Formula Y.

LIST OF ABBREVIATIONS USED IN THE EXAMPLES

EtOAc: ethyl acetate
HPLC: high performance liquid chromatography
TLC: thin-layer chromatography

EXAMPLES

Example 1

Synthesis of ethyl 9-(2-(benzyloxy)ethyl)-8-chloro-5-methoxy-2,3,4,9-tetrahydro-1H-carbazole-4-carboxylate Step 1: Synthesis of ethyl 3-bromo-2-oxocyclohexanecarboxylate

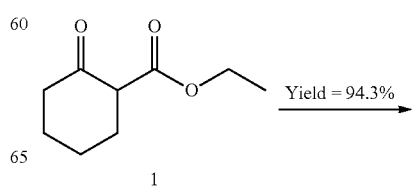

1

-continued

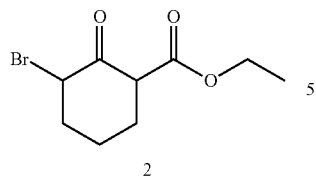
2

Step 2: Synthesis of N-(2-(benzyloxy)ethyl)-2-chloro-5-methoxyaniline

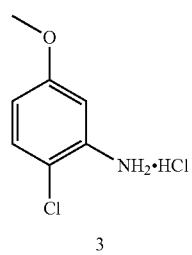 + 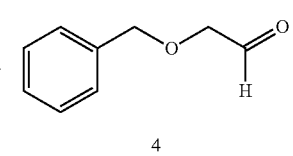 →

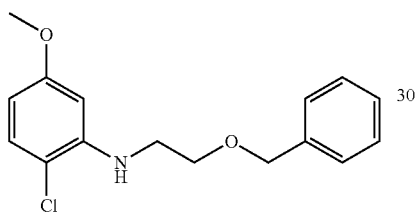
2.6 g
5

Step 3: Synthesis of ethyl 3-((2-(benzyloxy)ethyl)(2-chloro-5-methoxyphenyl)amino)-2-hydroxycyclohex-1-enecarboxylate

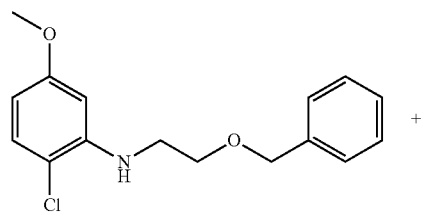 +

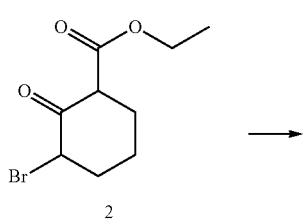
2

→

-continued

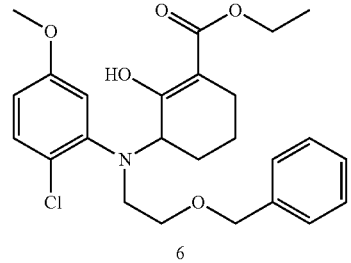
6

Step 4: Synthesis of ethyl 9-(2-(benzyloxy)ethyl)-8-chloro-5-methoxy-2,3,4,9-tetrahydro-1H-carbazole-4-carboxylate

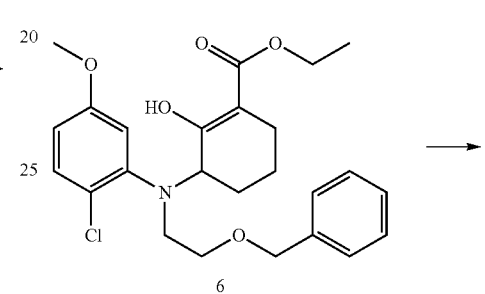
6

→

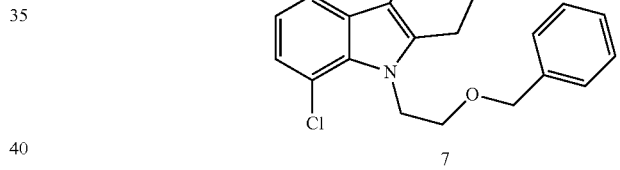
7

Each of steps 1-3 was carried out as described by Wadsworth et al (WO 2010/109007 Example 1).

For step 4 the general procedure used was firstly to charge compound 6 (x g, 1 mole equivalent) and diethyl ether (20 ml/g compound 6) under a nitrogen atmosphere. Zinc chloride was then added at ~1 g per gram of compound 6 and the reaction mixture heated to a good reflux and maintained at reflux for ~1 day. Then additional zinc chloride was added at ~0.5 g per gram of compound 6 and refluxed for a further ~1 day. A third addition of zinc chloride at 0.4-0.6 g per gram of compound 6 was carried out with reflux maintained with monitoring of the reaction with TLC (eluent 25% EtOAc in heptane, UV 254 nm), with the normal reaction time being approximately 5 days. Work up comprised evaporation of the reaction mixture (25-40° C.) under vacuum to obtain an oily mass. The crude was weighed and then dissolved in ethyl acetate (1-10 ml/g crude) and washed with HCl (1 part concentrated HCl and 5 parts water (approximately 2M), 2×1-10 ml/g crude). The ethyl acetate phase was then concentrated under vacuum at 25-50° C. and a sample withdrawn for TLC (eluent 25% EtOAc in heptane, UV 254 nm).

Storage at room temperature or below.

Table 1: shows the results of carrying out the cyclization step according to an embodiment of the present invention comprising multiple additions of zinc chloride wherein ~19-25 hours elapsed between each addition.

| Intermediate 6 (g) | ZnCl$_2$ (g) | Reaction time | HPLC purity | Isolated cyclized product (g) |
|---|---|---|---|---|
| 8.53 | 7.2 + 2.73 | 5 days | 87.20% | 7.79 |
| 3 | 3 + 1.5 + 1.5 | 5 days | 91% | 3.17 |
| 122 | 122 + 60 + 60 | 6 days | 89.90% | 117 |

The invention claimed is:

1. A method for the production of a compound of Formula Z:

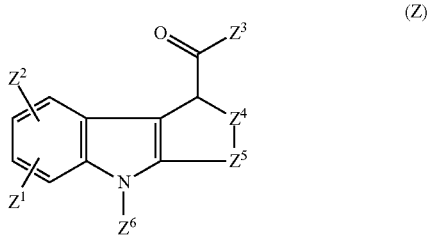

(Z)

wherein:
$Z^1$ is an $R^1$ group selected from halo or $C_{1-3}$ alkyl;
$Z^2$ is an $R^2$ group selected from hydrogen, hydroxyl, halo, cyano, $C_{1-3}$ alkyl, $C_{1-3}$ alkoxy, $C_{1-3}$ fluoroalkyl, or $C_{1-3}$ fluoroalkoxy;
$Z^3$ is an $R^3$ group selected from $C_{1-6}$ alkyl or —O—$R^7$ wherein $R^7$ is $C_{1-6}$ alkyl;
$Z^4$ is an $R^4$ group selected from O, S, SO, SO$_2$, or CH$_2$;
$Z^5$ is an $R^5$ group selected from CH$_2$, CH$_2$—CH$_2$, CH(CH$_3$)—CH$_2$ or CH$_2$—CH$_2$—CH$_2$;
$Z^6$ is the group —O—$R^8$ wherein $R^8$ is $C_{1-10}$ alkyl, $C_{3-12}$ aryl, $C_{7-14}$ arylalkyl, or a hydroxyl protecting group;
wherein said method of producing the compound of Formula Z comprises cyclizing of a compound of Formula Y:

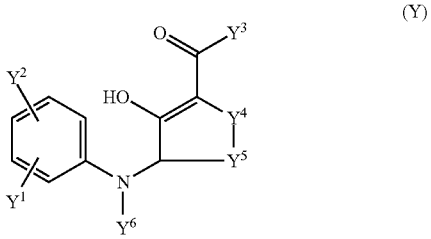

(Y)

wherein each of $Y^{1-6}$ are the same as each of $Z^{1-6}$; and
wherein said cyclizing is carried out by introduction of a zinc halide in a suitable solvent to a solution of said compound of Formula Y; and
wherein said introduction comprises a first addition and at least one subsequent addition of the zinc halide at an interval of at least 6 hours between two additions.

2. The method as defined in claim 1 wherein said $R^1$ group is at the bottom position of the aryl ring to which it is attached.

3. The method as defined in claim 1, wherein said $R^2$ group is at the top position of the aryl ring to which it is attached.

4. The method as defined in claim 1, wherein said $R^1$ group is halo.

5. The method as defined in claim 1, wherein said $R^2$ group is $C_{1-3}$ alkoxy, $C_{1-3}$ or $C_{1-3}$ fluoroalkoxy.

6. The method as defined in claim 1, wherein said $R^3$ group is —O—$R^7$ wherein $R^7$ is $C_{1-6}$ alkyl.

7. The method as defined in claim 6 wherein $R^7$ is $C_{1-3}$ alkyl.

8. The method as defined in claim 1, wherein $R^8$ is a hydroxyl protecting group.

9. The method as defined in claim 8, wherein $R^8$ is benzyl.

10. The method as defined in claim 9, wherein said zinc halide is zinc chloride.

11. The method as defined in claim 10 which further comprises conversion of the group —C(=O)—$Z^3$ of Formula Z to the group —C(=O)—$Z^{13}$ wherein $Z^{13}$ is hydroxyl or NR$^9$R$^{10}$ wherein R$^9$ and R$^{10}$ are independently $C_{1-3}$ alkyl, $C_{7-10}$ arylalkyl, or R$^9$ and R$^{10}$, together with the nitrogen to which they are attached, form a nitrogen-containing $C_{4-6}$ aliphatic ring optionally comprising 1 further heteroatom selected from nitrogen, oxygen and sulphur.

12. The method as defined in claim 11, which further comprises conversion of the group —N—$Z^6$ to the group —N—$Z^{16}$ wherein $Z^{16}$ is hydrogen, $C_{1-10}$ alkylene-OH or $C_{1-10}$ alkylene-LG wherein LG is a leaving group.

13. The method as defined in claim 12 wherein $Z^{16}$ is $C_{1-10}$ alkylene-LG.

14. The method as defined in either claim 13 wherein LG is halo, or an aryl or alkyl sulfonate.

15. The method as defined in claim 13 which further comprises conversion of the group —N—$Z^{16}$ to the group —N—$Z^{26}$ wherein $Z^{26}$ is $C_{1-10}$ alkylene-$^{18}$F.

* * * * *